United States Patent [19]

Rowland

[11] Patent Number: 4,803,471
[45] Date of Patent: Feb. 7, 1989

[54] VENTILATOR MONITOR AND ALARM APPARATUS

[75] Inventor: Robert O. Rowland, Hemet, Calif.

[73] Assignee: Hudson Oxygen Therapy Sales Co., Temecula, Calif.

[21] Appl. No.: 923,022

[22] Filed: Oct. 24, 1986

[51] Int. Cl.$^4$ ............................................. G08B 21/00
[52] U.S. Cl. ................................ 340/626; 128/202.22
[58] Field of Search ................................ 340/611, 626; 128/200.24, 202.22, 204.21, 204.23; 137/552.7, 624.11; 73/861.42, 861.47; 200/61.58 R, 81 R, 81.4, 83 R

[56] References Cited

U.S. PATENT DOCUMENTS 3,611,178  10/1971  McConnell ........................ 340/626
4,316,182   2/1982  Hodgson ........................ 128/204.21

Primary Examiner—Joseph A. Orsino
Assistant Examiner—Jill D. Jackson
Attorney, Agent, or Firm—Jerry R. Seiler

[57] ABSTRACT

An improved ventilator monitor and alarm apparatus includes circuit means for actuating the apparatus in response to sensed pressure in a ventilator circuit.

8 Claims, 3 Drawing Sheets

VENTILATOR MONITOR AND ALARM APPARATUS

BACKGROUND OF THE INVENTION

Ventilator monitor and alarm devices are used to monitor the presence of pressure in a ventilator circuit and give an alarm when that pressure fails or falls below a preselected minimum. Such monitor devices may be provided with a preset minimum pressure and a preset time delay after which time the alarm will be energized if the minimum pressure is not sensed in the circuit. The monitors may also be provided with means for adjusting the minimum pressure to be sensed with or without an adjustable time delay.

Although such monitor and alarm devices normally operate quite satisfactorily for their intended purpose when they are turned on, unfortunately sometimes a user inadvertently fails to activate the device. It is to the elimination of such a problem that the present invention is directed.

SUMMARY OF THE INVENTION

The ventilator monitor and alarm apparatus of the present invention includes, in addition to the functions of sensing a minimum selected pressure and a time delay, during which delay such minimum pressure must be detected to avoid actuating an alarm, an automatic switching feature for turning the apparatus on when pressure is sensed in the ventilator circuit. Such a device need simply be connected to the ventilator circuit, and even if it is not switched on by a user, will automatically turn itself on when the ventilator is operated.

DETAILED DESCRIPTION OF THE INVENTION

Figure 1:
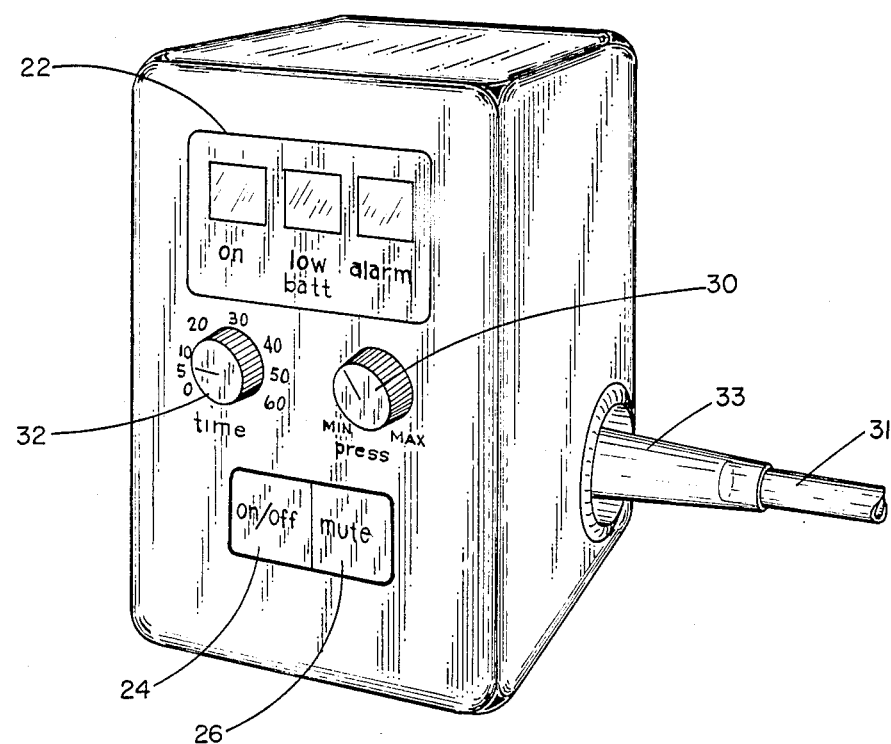
FIG. 1 is an exterior view of a ventilator monitor and alarm apparatus illustrating displays and actuation means.

In FIG. 1 there is illustrated a basic configuration of a ventilator monitor an alarm apparatus 20 which includes visual display functions 22, for example, an "on" light, a low battery light, and a visual alarm. Switch 24 manually turns the monitor on and off, and switch 26 is a mute button for silencing an audio alarm. Gas supply tubing 31 is connected to a fitting member 33 which communicates with a pressure sensing switch inside the apparatus case. The tubing is connected to a ventilator circuit and any pressure within the circuit is monitored by the pressure sensing switch.

Figure 2:
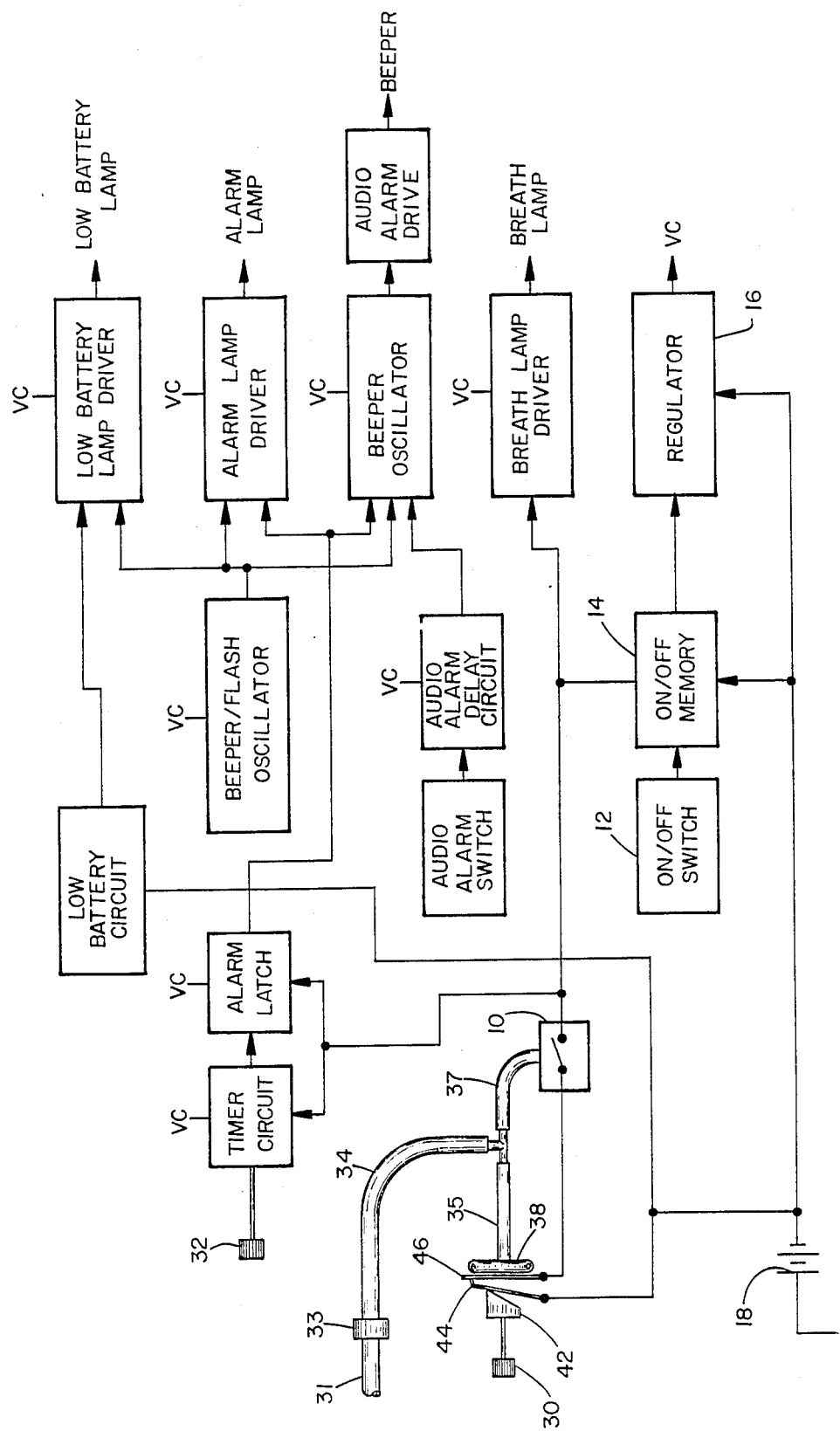
FIG. 2 is a block diagram illustrating the components of a suitable monitor and alarm apparatus according to the invention.

In FIG. 2 there is illustrated a block diagram representing the different components and showing their functions within the apparatus. In the preferred apparatus shown, the timer is adjustable, although a preset time delay may be incorporated instead, normally between about 10 and about 50 seconds. In the embodiment shown, both the delay time and minimum pressure are adjustable, time control knob 32 shown being adjustable from 0 to approximately 60 seconds, although such time may be, for example, up to 2 minutes or more, if desired. If the time delay adjustment is set on 0, when the minimum selected pressure is not sensed by the pressure sensing switch, the alarm is immediately actuated. On the other hand, where there is a preset time delay, whether it is built in to the timer circuit so that it is not adjustable or adjustable according to the preferred embodiment, it will prevent the alarm from sounding until the minimum pressure has not been sensed for the set time delay period. Moreover, each time pressure switch 10 closes in response to sensed minimum pressure, the timer circuit is reset.

In the preferred apparatus of FIG. 1, there is also a pressure adjustment control knob 30. Such a feature allows adjustment of the minimum pressure which must be sensed by the pressure sensor to prevent the alarm circuit to be energized. Such pressure adjustability normally will be between about 5 cm to about 60 cm $H_2O$. However, other upper and lower limits may be also incorporated into such an apparatus.

In the schematic diagram shown in FIG. 2, the pressure sensing feature is shown including the tubing 31 connected to the ventilator circuit and adapter 33 to which is connected tubing portions 34 and 37 for communicating with pressure sensing switch 10. The adjustable pressure sensing feature includes adjustment knob 30 which controls rotatable cam 42 against which rests movable plate 44 for touching plate 46 to close an electrical circuit. Moreover, diaphragm 38 expands by ventilator pressure via tubing 35 to urge plate 46 to make contact with the plate 44 to further prevent the alarm condition. When the circuit is closed, the alarm condition is prevented because the circuit between plates 44 and 46 is wired to pressure switch 10. The circuit will remain closed as long as there is sufficient ventilator pressure to cause the diaphragm to expand and force contact between the two plates 44 and 46. However, once ventilator pressure is below the selected minimum, the plates will no longer contact due to insufficient diaphragm inflation, thus opening the circuit at which time an alarm condition will begin as the timer circuit is actuated. If the minimum pressure is not sensed by the pressure switch during the time delay period, the alarm latch will actuate the alarms.

Figure 3:
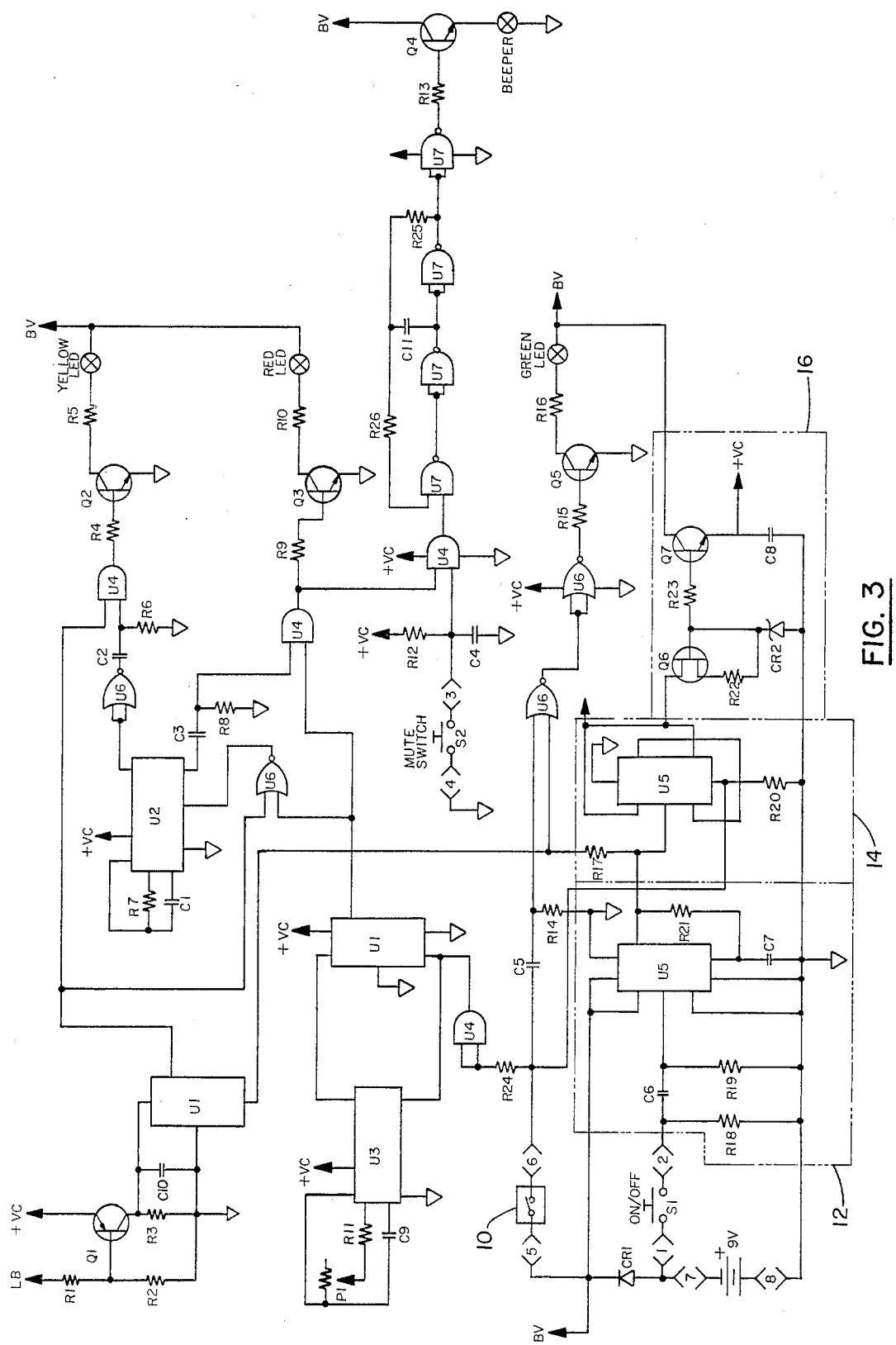
FIG. 3 is a detailed electronic schematic diagram of the electronics of a ventilator monitor of the invention.

The combination of the pressure switch 10 and on/off memory device 14 and on/off switch 12 are unique to the apparatus of the invention. These components and their connecting circuitry are shown in detail in FIG. 3. The apparatus may be turned on manually by an operator simply touching on/off switch 12. The on/off memory component comprises a logic circuit 14 cooperating with the pressure sensing switch 10 and is set to the "on" condition whenever any pressure is sensed by the pressure sensing switch in response to pressure in the ventilator circuit via tubing 31 and 34. This feature thus provides for operation of the apparatus independent of the on/off switch actuation. Thus, the device will function immediately when the ventilator which it is monitoring is operated without requiring an operator to switch the monitor and alarm apparatus "on". Battery 18 energizes the memory logic circuit 14 and regulator 16 in the "on" condition at all times while allowing the remainder of the apparatus components to "sleep" thereby substantially lowering unnecessary energy drain from the battery. The remaining components of the apparatus shown including the low battery circuit, audio/visual oscillator, low battery lamp driver, audio alarm switch, audio alarm delay circuit, alarm lamp driver, beeper flash oscillator, breath lamp driver and audio alarm driver are known features and components of such a ventilator monitor alarm apparatus and are shown in the electronic schematic of FIG. 3.

I claim:

1. A ventilator monitor and alarm apparatus including pressure sensing means for sensing ventilator pressure in a respiratory circuit, alarm means, and electronic circuit means including alarm circuit means cooperating with said pressure sensing means and said alarm means for creating an alarm condition and energizing said alarm in response to failure of said pressure sensing means to detect a preselected minimum pressure in said respiratory circuit, manual on/off switching means for turning the apparatus on and off, and a memory circuit which maintains said apparatus turned on until said manual on/off switching means is actuated to turn said apparatus off, comprising digital logic circuit means cooperating with said pressure sensing means for turning the apparatus on independent of said manual on/off switching means in response to a preselected minimum pressure sensed by said pressure sensing means said digital logic circuit means including means for monitoring the condition of said on/off switching means.

2. The monitor of claim 1 including a battery for operating said apparatus, and wherein said digital logic circuit means is maintained in an energized condition by said battery.

3. The monitor of claim 2 wherein said pressure sensing means includes adjustable means for selectively varying said preselected minimum pressure.

4. The monitor of claim 2 wherein said electronic circuit means includes timing means cooperating with said pressure sensing means and said alarm circuit means, said timing means causing a preselected time delay for energizing said alarm following a sensed alarm condition.

5. The monitor of claim 4 wherein said electronic circuit means includes alarm latch circuit means cooperating with said timing means for holding an alarm condition until a subsequent preselected minimum pressure is sensed by said pressure sensing means.

6. The monitor of claim 5 wherein said timing means includes adjustable means for selectively varying said preselected time delay.

7. The monitor of claim 3 wherein said electronic circuit means includes timing means cooperating with said pressure sensing means and said alarm circuit means, said timing means causing a preselected time delay for energizing said alarm following a sensed alarm condition.

8. The monitor of claim 7 wherein said timing means includes adjustable means for selectively varying said preselected time delay.

* * * * *